United States Patent [19]

Kabbe et al.

[11] 3,995,044
[45] Nov. 30, 1976

[54] PYRIDINE CARBOXYLIC ACID AMIDES FOR MYCOBACTERIUM INFECTIONS

[75] Inventors: Hans-Joachim Kabbe, Leverkusen; Hinrich Otten, Wuppertal; Karl Heinrich Mayer, Opladen-Quettingen; Erich Klauke, Odenthal-Hahnenberg, all of Germany

[73] Assignee: Bayer Aktiengesellschaft, Germany

[22] Filed: June 3, 1975

[21] Appl. No.: 583,464

[30] Foreign Application Priority Data

June 14, 1974 Germany............................ 2428673

[52] U.S. Cl................................ 424/263; 424/246; 424/250; 424/251; 424/258; 424/262; 424/267; 424/269; 424/270; 424/272; 424/274; 424/275; 424/276; 424/278; 424/283; 424/285; 260/302 A; 260/307 R; 260/307 H; 260/308 A; 260/308 B; 260/309; 260/239 BF; 260/213 R; 260/309.6; 260/243 B; 260/244 R; 260/310 R; 260/247.2 A; 260/250 B; 260/326 A; 260/250 Q; 260/251 R; 260/326.1; 260/265; 260/287 R; 260/326.2; 260/287 D; 260/295 AM; 260/327 R; 260/295 B; 260/302 R; 260/332.2 A; 260/333; 260/340.2; 260/345.7; 260/347.3

[51] Int. Cl.²......................................... A61K 31/44
[58] Field of Search .. 260/294.9, 295 AM, 295.5 A; 424/266, 263

[56] References Cited

UNITED STATES PATENTS

| | | | |
|---|---|---|---|
| 3,270,026 | 8/1966 | Berger et al................. | 260/295 AM |
| 3,367,940 | 2/1968 | Hotten........................ | 260/295 AM |
| 3,439,019 | 4/1969 | Sarett et al.................. | 260/295 AM |
| 3,455,940 | 7/1969 | Stecker....................... | 260/295 AM |
| 3,509,166 | 4/1970 | Wright, Jr. et al. ......... | 260/295 AM |
| 3,676,447 | 7/1972 | Skinner et al. .............. | 260/295 AM |

Primary Examiner—Norman A. Drezin

[57] ABSTRACT

Benzoic acid amides characterized by the presence of a nitro, cyano, trifluoromethyl, alkylsulfonyl, carboxy, carbalkoxy, amido or sulfonamido substituent in the phenyl ring and by the presence of a heterocyclic group connected to the amide nitrogen atom through a hydrocarbon chain are antibacterial agents and in particular antituberculosis agents. The compounds, of which N-(pyrid-2-yl-methyl)3,5-dinitrobenzoic acid amide is a typical embodiment, are prepared by the reaction of an appropriately substituted benzoic acid, or derivative thereof, with an appropriate amine.

11 Claims, No Drawings

PYRIDINE CARBOXYLIC ACID AMIDES FOR MYCOBACTERIUM INFECTIONS

DETAILED DESCRIPTION

The present invention pertains to novel benzoic acid amides, to processes for their preparation and their use as antimicrobial substances, especially as anti-tuberculosis agents.

While some fourteen medicaments active against tuberculosis are known, it has not yet proved possible to develop a reliable scheme of chemotherapy. Instead, it has always been necessary to carry out a multiple therapy; i.e., three or more anti-tuberculosis active compounds of different mechanisms of action are combined, in accordance with the particular circumstances of the patient. The fourteen types of anti-tuberculosis active compounds clinically in use can be divided into nine groups on the basis of the parallel resistance which in part exists between them, from which a three drug combination scheme, or in cases presenting special problems up to five drug combination scheme, for the individual patient can be composed. Since the commercially available agents against tuberculosis show side effects in up to 30% of the patients, it is understandable that carrying out a complete tuberculosis therapy also presents very great problems in relation to the tolerance of the medicaments. As a result, there is a demand for new agents against tuberculosis which either display new mechanisms of action against mycobacteria or display better tolerance; see, e.g. E. Freerksen in R. Haussen: Blasige Lungenkranheiten; poststenotisches Bronchosyndrom; Alveolare Proteinose; Tuberkulostatika zweiter Ordnung [Vesicular Diseases of the Lungs; Poststenotic Bronchosyndrome; Alveolar Proteinosis; Second Order Tuberculostatic Agents], Georg Thieme Verlag, Stuttgart, 1968, 141 – 152.

The present invention pertains to benzoic acid amides of the formula:

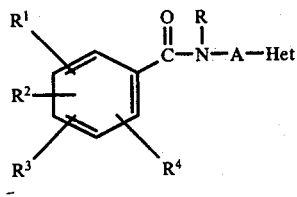

wherein

R is hydrogen, alkyl, aryl, aralkyl or a heterocyclic (lower alkyl) radical;

$R^1$ is nitro, cyano, trifluoromethyl, lower alkylsulfonyl, carboxy, carbo(lower alkoxy)

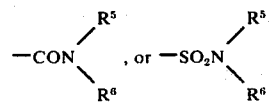

in which each of $R^5$ and $R^6$, independent of the other, is hydrogen, lower alkyl, aryl, aralkyl or a heterocyclic (lower alkyl) radical;

$R^2$ is hydrogen or a group as defined for $R^1$;

each of $R^3$ and $R^4$, independent of the other, is hydrogen, halo or lower alkyl;

A is alkylene or alkylene substituted by pyridyl or aryl; and

Het is a heterocyclic radical unsubstituted or substituted by halo, lower alkyl, lower alkoxy or aryl;

or a salt thereof when one or more of R, $R^1$, $R^2$, A and Het comprises a basic or acidic group.

The salts embraced by the present invention are those which are pharmaceutically acceptable and not toxic and include acid addition salts when the compounds of the invention bear at least one basic nitrogen atom or amino group and the alkali metal, alkaline earth metal and amine salts when the compounds of the invention bear at least one free carboxy group.

The benzoic acid amides of Formula I and their salts have anti-tuberculosis properties. Chemically these compounds are characterized by (a) at least one nitro, cyano, trifluoromethyl, alkylsulfonyl, carboxy, carbalkoxy, amido or sulfonamido group in the aromatic ring of the benzoic acid amide, optionally with further substitution in this ring, and (b) a heterocyclic group linked to the nitrogen atom of the amide through a hydrocarbon chain (A).

In one embodiment of the invention, the heterocyclic group designated by Het is a mono- or bi-cyclic ring system of 5 to 12 ring atoms, one of said ring atoms being oxygen, sulfur or nitrogen, 0 to 2 of the then remaining ring atoms being nitrogen, and all of the then remaining ring atoms being carbon, said ring system being unsubstituted or substituted by halo, lower alkyl, lower alkoxy, phenyl or halophenyl.

In a further embodiment of the invention, the ring system of Het is monocyclic and contains 5 ring atoms, as for example, the ring systems of furan, thiophene, pyrrole, oxazole, isoxazole, thiazole, isothiazole, pyrazole, imidazole or triazole, including the corresponding dihydro and tetrahydro forms of these ring systems.

In a further embodiment of the invention, the ring system of Het is monocyclic and contains 6 ring atoms, as for example, those of pyran, pyridine, oxazine, thiazine, pyrazine, or pyrimidine, including the corresponding dihydro, tetrahydro and hexahydro forms of these ring systems.

In another embodiment of the invention, the ring system of Het is monocyclic and contains 7 ring atoms, as for example, the ring systems of azepine, oxepin or thiepin, including the corresponding dihydro, tetrahydro and hexahydro forms of these ring systems.

In another embodiment of the invention, the ring system of Het is bicyclic and contains 9 ring atoms, as for example, the ring systems of indole, isoindole, benzofuran, benzothiophene, benzimidazole and indazole, including the corresponding dihydro, tetrahydro, hexahydro and octahydro forms of these ring systems.

In another embodiment of the invention, the ring system of Het is bicyclic and contains 10 ring atoms, as for example, the ring systems of quinoline, isoquinoline, phthalazine, naphthyridine, quinoxaline, quinazoline or cinnoline, including the corresponding dihydro, tetrahydro, hexadyro, octahydro and decahydro forms of these ring systems.

In another embodiment of the invention,

R is hydrogen, lower alkyl, phenyl(lower alkyl) or pyridyl(lower alkyl);

$R^1$ is nitro, cyano, trifluoromethyl, (lower alkyl)sulfonyl, carboxy, carbo(lower alkoxy), carbamyl, N-(lower alkyl)carbamyl, or N-[pyridyl(lower alkyl)]carbamyl;

R₂ is hydrogen, nitro, cyano, trifluoromethyl, (lower alkyl)sulfonyl, carboxy, carbo(lower alkoxy), carbamyl, N-(lower alkyl)carbamyl, or N-[pyridyl(lower alkyl)]carbamyl;

each of R³ and R⁴, independent of the other, is hydrogen, halo or lower alkyl;

A is alkylene of 1 to 4 carbon atoms or benzylidene.

In another embodiment of the invention,

R is hydrogen, methyl, ethyl, benzyl or pyridylmethyl;

R¹ is nitro, cyano, trifluoromethyl, methylsulfonyl, carboxy, carbomethoxy or carbethoxy;

R² is hydrogen, nitro, cyano, trifluoromethyl, methylsulfonyl, carboxy, carbomethoxy or carbethoxy;

each of R³ and R⁴, independent of the other, is hydrogen, chloro, bromo or methyl; and A is methylene, ethylene, ethylidene, trimethylene or benzylidene.

Lower alkyl groups for R, R³, R⁴, R⁵, R⁶ in the above formulas, and for R⁷, R⁸ mentioned later, and for the optional substituents on Y are straight or branched monovalent hydrocarbon chains with 1 to 6, especially 1 to 4, carbon atoms, as for example methyl, ethyl, n- and i-propyl and n-, i- and t-butyl.

Lower alkoxy groups are such lower alkyl groups with 1 to 6, especially 1 to 4, carbon atoms joined through an ethereal oxygen atom. Methoxy, ethoxy, n- and i-propoxy and n-, i- and t-butoxy can be mentioned as examples.

Lower alkylene groups embraced by A are those straight and branched chains having 1 to 6 carbon atoms with from 1 to 3 carbon atoms between the valence bonds. Methylene, ethylene, propylene, methylmethylene, ethylidene, 1- or 2-methylethylene, phenylmethylene and 2-pyridylmethylene may be mentioned as examples.

Lower alkylsulphonyl groups contain 1 to 6, especially 1 or 2, carbon atoms. Methylsulphonyl, ethylsulphonyl, n- and i-propylsulphonyl and n-, i- and t-butylsulphonyl may be mentioned as examples.

Preferred alkoxycarbonyl groups [carbo(lower alkoxy)] contain 1 to 6, especially 1 or 2, carbon atoms in the alkoxy part. Methoxycarbonyl, ethoxycarbonyl, n- and i-propoxycarbonyl and n-, i- and t-butoxycarbonyl may be mentioned as examples.

Preferred aralkyl groups for R, R⁵, R⁶, and R⁸, mentioned subsequently, contain 6 or 10, especially 6, carbon atoms in the aryl part and 1 to 6, preferably 1 to 4 and especially 1 or 2, carbon atoms in the alkyl part, which part can be straight or branched chain. Benzyl and phenylethyl can be mentioned as examples.

Preferred aryl groups for the radicals R, R⁵, R⁶, R⁷ and R⁸, and the optional substituent on A and Het, contain 6 to 10 carbon atoms in the aryl part. Phenyl and naphthyl can be mentioned as examples.

Het represents a 5- to 10-membered, (usually 5-membered or 6-membered when monocyclic) saturated or unsaturated heterocyclic ring system with 1 to 3, usually 1 or 2, identical or different hetero atoms, such as oxygen, sulphur and/or nitrogen. The heterocyclic radical can contain one or more, preferably 1 to 3, especially 1 or 2, identical or different substituents. If aryl radicals such as phenyl are present as substituents, these can in turn be substituted by 1 to 3, preferably 1 or 2, halogen atoms, such as chlorine, fluorine or bromine, preferably chlorine and bromine, alkyl groups with 1 to 4 carbon atoms, preferably methyl or ethyl, alkoxy groups with 1 to 4 carbon atoms, preferably methoxy or ethoxy, nitro, cyano and/or trifluoromethyl radicals. The heterocyclic radical can also carry a fused benzo ring which can be substituted in the same way as the aryl radical. The following are examples of such heterocyclic ring systems: furyl, tetrahydrofuryl, 5-methylfuryl, 5-(3',4'-dichlorophenyl)-furyl, thienyl, pyrrolyl, pyrrolidinyl, imidazolyl, pyrazolyl, triazolyl, oxazolyl, isoxazolyl, thiazolyl, 4-methylthiazolyl, isothiazolyl, oxadiazolyl, pyranyl, dihydropyranyl, pyridyl, 2,6-dimethylpyridinyl, pyridazyl, pyrimidinyl, pyrazinyl, piperazinyl, oxazinyl, isoxazinyl, azepinyl, oxepinyl, thiepinyl, indolyl, benzimidazolyl, benzoxazolyl, quinolyl, tetrahydroquinolyl, isoquinolyl, quinazolyl, quinoxalyl, cinnolyl and indazolyl.

Halogeno denotes fluoro, chloro, bromo and iodo, preferably fluoro, chloro and bromo and especially chloro and bromo.

The invention also provides a method of preparing the benzoic acid amides of Formula I and their salts which comprises a. reacting an acid halide of the formula:

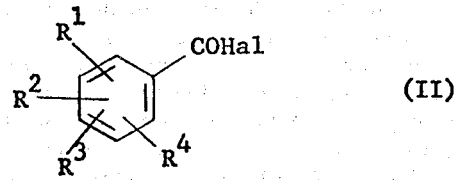

in which R¹, R², R³ and R⁴ are as defined above; and

Hal represents a chlorine or bromine atom with an amine of the formula:

in which R, A and Het are as defined above, optionally in the presence of acid-binding agents;

b. reacting a carboxylic acid of the formula:

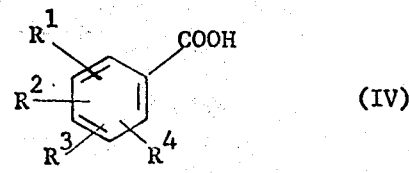

in which R¹, R², R³ and R⁴ are as defined above, with an amine of Formula III in the presence of an agent which split off water;

c. reacting a carboxylic acid ester of the formula:

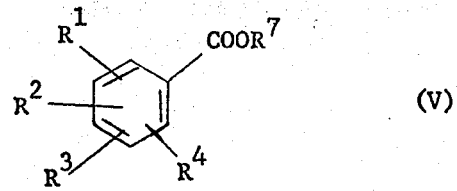

in which R¹, R², R³ and R⁴ are as defined above; and

R⁷ is alkyl or aryl, with an amine of Formula III, with elimination of R⁸OH; or d. reacting an anhydride of the formula:

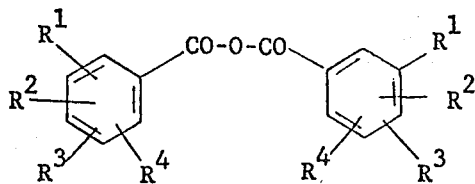

(VI)

or

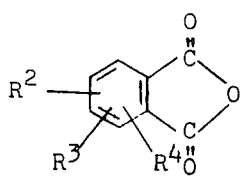

(VII)

in which $R^1$, $R^2$, $R^3$ and $R^4$ are as defined above, with an amine of Formula III.

A modification of the last of these reactions involves the use of a phthalic acid anhydride (VII); i.e. an anhydride of an acid of Formula IV in which $R^1$ is a carboxy group in the ortho-position, in lieu of the anhydride of Formula VI.

In addition to the foregoing processes, one can also effect various interconversions with the final compounds. Carbalkoxy groups can thus be converted into carboxy or aminocarbonyl groups, salts can be formed, or compounds obtained as salts can be converted to their non-salt form.

The acids of Formula IV used as starting materials are known in most cases and can be converted in accordance with known methods into acid halides of Formula II, esters of Formula V and anhydrides of Formula VI and VII. The following can be mentioned as examples: 2-nitrobenzoic acid, 3-nitrobenzoic acid, 4-nitrobenzoic acid, 2-trifluoromethylbenzoic acid, 3-trifluoromethylbenzoic acid, 4-trifluoromethylbenzoic acid, 3-cyanobenzoic acid, 2-nitro-5-methylbenzoic acid, 2-methoxycarbonylbenzoic acid, 2,4-dinitrobenzoic acid, 3,5-dinitrobenzoic acid, 3-nitro-5-trifluoromethylbenzoic acid, 2-chloro-3,5-dinitrobenzoic acid, 2,4-dichloro-3,5-dinitrobenzoic acid, 2,6-dichloro-3,5-dinitrobenzoic acid, 3,5-bis-trifluoromethylbenzoic acid, 2,4-bis-trifluoromethylbenzoic acid, 3,5-dicyanobenzoic acid, 3-nitro-5-cyanobenzoic acid, 2-methyl-3,5-dinitrobenzoic acid, 3-methylsulphonyl-5-cyanobenzoic acid, 3-methylsulphonyl-5-nitrobenzoic acid, 3-methoxycarbonyl-5-nitrobenzoic acid, 3-butoxycarbonyl-5-nitrobenzoic acid, 3-α-pyridylmethylaminocarbonyl-5-nitrobenzoic acid, 3,5-diacetylbenzoic acid, 3-benzoyl-5-nitrobenzoic acid, 3-benzoyl-5-cyanobenzoic acid, 5-nitroisophthalic acid and the corresponding anhydrides, chlorides, bromides and methyl, ethyl, n- and i-propyl, n-, i- and t-butyl and phenyl esters.

The amines III used as starting materials are also known or can be prepared according to generally known methods, for example by reaction of halogenoalkylheterocyclic compounds of the formula:

$$\text{Hal—A—HET} \qquad (VIII)$$

in which
Hal is bromine, chlorine or iodine and
A and Het are as defined above, with amines of the formula:

$$\text{R—NH}_2 \qquad (IX)$$

in which
R is as defined above,
or by hydrogenation of nitriles of the formula:

$$\text{Het—CN} \qquad (X)$$

in which
Het is as defined above,
or by hydrogenation of carbonyl compounds of the formulas XI and XII:

$$\text{Het—CHO} \qquad (XI)$$

$$\text{Het—CO—R}^8 \qquad (XII)$$

in which
$R^8$ is alkyl, aryl or aralkyl, and
Het is as defined above,
in the presence of ammonia.

The following may be mentioned as examples of amines of the Formula III: 2-, 3- and 4-aminomethylpyridine, 2-, 3- and 4-aminomethylquinoline, 1-amino-2-(α-pyridyl)-ethane, 1-amino-2-(β-pyridyl)-ethane, 1-amino-2-(γ-pyridyl)-ethane, 1-amino-1-(α-pyridyl)-ethane, 1-amino-1-(β-pyridyl)-ethane, 1-amino-1-(γ-pyridyl)-ethane, 1-amino-2-(γ-pyridyl)-propane, 2-amino-methyl-6-methylpyridine, 3-aminomethyl-1,2,3,4-tetrahydroquinoline, 2-aminosulpholane, N-benzyl-N-(2-pyridyl)-methylamine, N-ethyl-N-(2-pyridyl)-methylamine, 2-aminomethylfurane, α-(2-aminoethyl)-furane, α-(1-aminoethyl)-furane, 2-pyridylphenylmethylamine, N-di-(2-pyridyl)-amine, N-di-(4-pyridyl)-amine, (N-pyrrolyl)-propylamine, 2-aminomethyltetrahydrofurane, 2-aminomethyldihydropyrane, α-(2-aminoethyl)indole, 2-aminomethyl-5-methylfurane, 2-aminomethylbenzimidazole, 2-aminomethyl-5-(3,4-dichlorophenyl)-furane, 2-(β-aminoethyl)-4-methylthiazole, 1-(β-aminoethyl)-triazole-(1,2,3), N-methyl-N'-aminopropylpiperazine, N-aminoethylthiomorpholine dioxide, N-aminopropylmorpholine, 2-aminomethylpyrazine, 3-aminomethylindazole, aminoethylpyrrolidine, N-aminopropylindoline, N-aminoethylinodoline, N-aminopropylhexamethyleneimine and 2-aminomethyl-1,4-benzodioxane.

Diluents which can be used in process variants (a) to (d) are generally inert organic solvents. These include hydrocarbons such as benzene, toluene and xylene, halogenohydrocarbons such as chloroform, carbon tetrachloride, chlorobenzene and dichlorobenzene, ethers such as diethyl ether, tetrahydrofuran and dioxane, amides such as dimethylformamide, esters such as ethyl acetate, nitriles such as acetonitrile and propionitrile and ketones such as methyl isobutyl ketone.

All customary acid-binding agents can be used as acid binders in process variant (a). They include the alkali metal hydroxides such as sodium hydroxide or potassium hydroxide, alkali metal carbonates, such as sodium carbonate and potassium carbonate, alkali metal bicarbonates such as sodium bicarbonate and potassium bicarbonate and organic bases for example organic amines such as pyridine, triethylamine and tributylamine.

In process variant (b), it is possible to utilize any of the customary agents which split off water and which are employed for the preparation of amides from acids and amines, as for example carbodiimides such as dicyclohexylcarbodiimide or inorganic acid chlorides, such as phosphorus oxychloride or thionyl chloride.

Process variant (c) can optionally also be carried out without diluents.

In all process variants (a) to (d) the reaction temperature can be varied within a considerable range. In the case of the process variants mentioned under (a), (b) and (d), the reaction is usually carried out at between about $-20°$ C and $+100°$ C, preferably between $0°$ C and $+50°$ C. Process variant (c) in general requires higher temperatures, usually between about $20°$ C and $250°$ C and preferably $100°$ C to $200°$ C.

The reactions can be carried out under normal pressure, especially process variants (a) and (b), and also under elevated pressure as for example in the case of process variant (c).

In carrying out the process according to the invention, the particular starting materials of Formulas II, IV, V, VI and VII and those of Formula III are preferably reacted in the molar ratio of 1.2:1 to 1:1.2, but in the case of very valuable starting materials it is, for example, also possible to choose molar ratios from 5:1 to 1:5 to achieve good yields. The molar ratios can thus vary within very wide ranges without having a particular adverse influence on the result. The acid binders in process variant (a) are preferably employed in a molar equivalent amount, that is to say in an amount sufficient to bind the acid produced. However, in some cases it can be advisable to employ a smaller amount, or preferably a larger amount, of acid-binder.

If the compounds of Formula I contain alkoxycarbonyl groups, these can be converted into carboxyl or aminocarbonyl groups in accordance with generally known methods. Alkoxycarbonyl groups can, for example, be converted into carboxyl groups with alkalis such as sodium hydroxide, in aqueous alcoholic solution at room temperature or elevated temperature.

If the compounds of Formula I contain nitro groups, these can be reduced to amino groups in accordance with generally known methods. The hydroxyl or amino groups contained in the compounds of Formula I can be alkylated or acylated in accordance with known methods. The compounds according to the invention are isolated and purified if desired, in accordance with generally customary methods.

The carboxylic acid amides according to the invention can, if they contain a basic nitrogen atom in an amino substitute or heterocyclic ring or an acidic substituent, also be used in the form of their salts, with acids or bases, respectively. As examples of such acids forming acid addition salts there may be mentioned sulphonic acids such as toluenesulphonic acid, naphthalenesulphonic acid and naphthalenedisulphonic acid, carboxylic acids such as acetic acid, benzoic acid, lactic acid, citric acid and hydroxynapthoic acid and hydrogen halide acids such as hydrochloric acid and hydrobromic acid. As examples of bases suitable for forming salts there may be mentioned alkali metal bases such as sodium hydroxide solution and potassium hydroxide, alkaline earth metal bases, and organic amines such as dicyclohexylamine, triethylamine and diethanolamine. The compounds of Formula I can be converted into the salts in accordance with generally customary methods. The hydrohalides of the compounds of Formula I are also obtained if process variant (a) is followed and no acid-binding agent is added. The salts are isolated and purified in accordance with generally customary methods.

The following may be mentioned individually as new active compounds: N-[furyl-(2)-methyl]-3,5-dinitro-benzoic acid amide, N-[5-methyl-furyl-(2)-methyl]-N-methyl-3,5-dinitro-benzoic acid amide, N-[5-(3',4'-dichlorophenyl)furyl-(2)-methyl]-3,5-dinitro-benzoic acid amide, N-[furyl-(2)-1,2-ethyl]-3,5-dinitro-benzoic acid amide, N-[furyl-(2)-1,1-ethyl]-3,5-dinitro-benzoic acid amide, N-[tetrahydrofuryl-(2)-methyl]-3,5-dinitro-benzoic acid amide, N-[thienyl-(2)-methyl]-3,5-dicyano-benzoic acid amide, N-[pyrrolyl-(1)-1,3-propyl]-3,5-dinitro-benzoic acid amide, N-[tetrahydropyrrolyl-(1)-methyl]-3,5-bis-trifluoromethyl-benzoic acid amide, N-[imidazolyl-(2)-1,2-propyl]-3,5-bis-(methylsulphonyl)-benzoic acid amide, N-[pyrazolyl-(3)-2,1-propyl]-3,5-bis-(methoxycarbonyl)-benzoic acid amide, N-[1,2,3-triazolyl-(1)-1,2-ethyl]-3,5-dinitro-benzoic acid amide, N-[oxazolyl-(2)-methyl]-3,5-bis-(dimethylaminocarbonyl)-benzoic acid amide, N-[isoxazolyl-(3)-methyl]-3,5-bis-(diethylaminosulphonyl)-benzoic acid amide, N-[4-methyl-thiazolyl-(2)-1,2-ethyl]-3,5-dinitro-benzoic acid amide, N-[$\Delta^2$-dihydro-pyranyl-(6)-methyl]-3,5-dinitro-benzoic acid amide, N-[tetrahydropyrazyl-(1)-1,3-propyl]-3-nitro-5-cyanobenzoic acid amide, N-[pyridyl-(2)-methyl]-3,5-dinitro-benzoic acid amide, N-[pyridyl-(2)-methyl]-3,5-bis-(trifluoromethyl)-benzoic acid amide, N-[pyridyl-(2)-methyl]-2,4-bis-(trifluoromethyl)benzoic acid amide, N-[pyridyl-(2)-methyl]-3-carboxy-5-nitrobenzoic acid amide, N-[pyridyl-(2)-methyl]-2,4-dinitro-benzoic acid amide, N-[pyridyl-(2)-methyl]-3-nitro-5-trifluoromethylbenzoic acid amide, N-[pyridyl-(2)-methyl]-5-methoxycarbonyl-3-nitro-benzoic acid amide, N-[pyridyl-(2)-methyl]-3-nitro-5-pyridyl-(2)-methylaminocarbonyl-benzoic acid amide, N-[pyridyl-(2)-methyl]-N-benzyl-3,5-dinitro-benzoic acid amide, N-[pyridyl-(2)-methyl]-N-ethyl-3,5-dinitro-benzoic acid amide, N,N-bis-[pyridyl-(2)-methyl]-3,5-dinitro-benzoic acid amide, N-[pyridyl-(2)-1,2-ethyl]-3,5-dinitro-benzoic acid amide, N-[pyridyl-(2)-1,1-ethyl]-3,5-dinitro-benzoic acid amide, N-[pyridyl-(2)-1,1-benzyl]-3,5-dinitro-benzoic acid amide, N-[6-methyl-pyridyl-(2)-methyl]-3,5-dinitro-benzoic acid amide, N-[pyridyl-(3)-methyl]-3,5-dinitro-benzoic acid amide, N-[pyridyl-(4)-methyl]-3,5-dinitro-benzoic acid amide, N-[pyridyl-(4)-methyl]-4-chloro-3-nitro-benzoic acid amide, N-[quinolyl-(2)-methyl]-3,5-dinitro-benzoic acid amide, N-[quinolyl-(3)-methyl]-3,5-dinitro-benzoic acid amide, N-[tetrahydro-quinolyl-(2)-methyl]-3,5-dinitro-benzoic acid amide, N-[$\Delta^2$-dihydro-quinolyl-(3)-1,2-ethyl]-3,5-dinitrobenzoic acid amide, N-[benzimidazolyl-(2)-methyl]-3,5-dinitrobenzoic acid amide, N-[pyridazyl-(3)-methyl]-2,4-bis-(carboxy)-benzoic acid amide, N-[pyrimidyl-(2)-methyl]-3,5-bis-(trifluoromethyl)-benzoic acid amide, N-[pyrazyl-(2)-1,3-propyl]-3,5-dicyano-benzoic acid amide, N-[4-methyl-tetrahydro-pyrazyl-(1)-methyl]-3,5-dinitro-benzoic acid amide, N-[tetrahydro-oxazyl-(4)-1,3-propyl]-3,5-dinitro-benzoic acid amide, N-[tetrahydro-thiazyl-1,1-dioxide-(4)-methyl]-3,5-dinitro-benzoic acid amide, N-[azepinyl-(2)-methyl]-3,5-bis-(ethylsulphonylmethyl)-benzoic acid amide, N-[indolyl-(3)-1,3-propyl]-2,4-bis-(methylcarbonyl)-benzoic acid amide, N-[indazolyl-(3)-methyl]-3-nitro-5-cyano-benzoic acid amide, N-[benzthiazolyl-(2)-methyl]-3-trifluoromethyl-5-methylsulphonyl-benzoic acid amide, N-[quinoxalyl-(2)-methyl]-N-ethyl-3-nitro-5-bis- (dimethylaminosulphonyl)-benzoic acid amide, N-[pyridyl-(2)-methyl]-2-nitro-benzoic acid amide, N-[pyridyl-(2)-methyl]-3-nitro-benzoic acid amide, N-[pyridyl-(2)-methyl]-4-nitro-benzoic acid amide, N-[pyridyl-(2)-methyl]-2-trifluoro-methyl-benzoic acid amide, N-[pyridyl-(2)-methyl]-3-trifluoro-methyl-benzoic acid amide, N-[pyridyl-(2)-methyl]-4-trifluoro-methyl-benzoic acid amide, N-[pyridyl-(2)-methyl]-3-cyano-benzoic acid amide, N-[pyridyl-(2)-methyl]-3-methoxycarbonyl-benzoic acid amide, N-[pyridyl-(2)-carboxy-benzoic acid amide, N-[pyridyl-(2)-methyl]-2-nitro-3-chlorobenzoic acid amide, N-[pyridyl-(2)-methyl]-6-chloro-3-methylsulphonyl-benzoic acid amide, N-[pyridyl-(2)-methyl]-5-bromo-3-nitro-benzoic acid amide, N-[pyridyl-(2)-methyl]-6-chloro-3,5-dinitro-benzoic acid amide, N-[pyridyl-(2)-methyl]-3,5-dinitro-2-methyl-benzoic acid amide, N-[pyridyl-(2)-methyl]-2,6-dichloro-3,5-dinitro-benzoic acid amide, N-[pyridyl-(2)-methyl]-2,4-dichloro-3,5-dinitro-benzoic acid amide, N-[pyridyl-(3)-methyl]-4-ethylsulphonyl-benzoic acid amide, N-[pyridyl-(3)-methyl]-2-nitro-benzoic acid amide, N-[pyridyl-(3)-methyl]-3-cyano-benzoic acid amide, N-[pyridyl-(3)-methyl]-4-butoxycarbonyl-benzoic acid amide, N-[pyridyl-(3)-methyl]-2,4-bis-(methylcarbonyl)-benzoic acid amide, N-[pyridyl-(4)-methyl]-3-trifluoromethyl-benzoic acid amide, N-[pyridyl-(4)-methyl]-3,5-dinitro-2-methyl-benzoic acid amide, N-[pyridyl-(4)-methyl]-4-chloro-3,5-dinitro-benzoic acid amide, N-[pyridyl-(4)-methyl]-2-chloro-3,5-dinitro-benzoic acid amide, N-[pyridyl-(4)-methyl]-2-chloro-3,5-dicyano-benzoic acid amide, N-[pyridyl-(2)-methyl]-3-cyano-5-nitro-benzoic acid amide and N-[pyridyl-(2)-methyl]-3,5-dicyano-benzoic acid amide.

The antibacterial activity of the compounds, in particular their excellent activity against mycobacteria, can be conveniently observed in known in vitro and in vivo models.

For the in vitro experiments, Löwenstein-Jensen egg medium was used as the culture medium and Difco-Tb-Bouillon (slightly modified: no added albumin, but 0.2% added agar) was used as the semi-synthetic fluid medium.

The active compounds, in predetermined concentration steps of 128 mcg/ml, decreasing by a dilution factor of 2, were added to the media. The culture test tubes were inoculated with the international test strain *Mycobacterium tuberculosis* strain H37Rv and with other *M. tuberculosis* strains isolated from material obtained from patients and showing different degrees of resistance to tuberculotic agents. In order to delimit the anti-mycobacterial spectrum of action, the action against so-called "atypical mycobacteria", which were classified in accordance with the generally customary Runyon scheme, was tested.

The animal experiments were above all carried out with white mice (CFI breed, Winkelmann, Kirchborchen) infected with Mycobacterium tuberculosis H37Rv. After intravenous infection with $10^4$–$10^5$ germ units/mouse, an oral or subcutaneous treatment was carried out once daily for a period of 2 weeks (that is to say 5 times per week). At predetermined intervals of time (11th, 14th and 17th day after infection) mice from the treatment groups were killed, the spleens were removed and standardised smear preparations were produced from the homogenate; the tubercle germ content in these was evaluated by means of fluorescence microscopy. The reduction in the number of germs detectable in the treatment groups, in comparison to the infected control group which did not receive chemotherapeutic treatment, is taken as an expression of the chemotherapeutic effect of the particular active compound. If, as the result of very low germ counts, the limit of microscopic detection is reached in the method, the recorded value shows a germ reduction of 100% as the best value; correspondingly, if the number of germs of a treatment group is the same as that of the control group, the reduction is 0%. The values obtained are grouped together in 5 rating groups and give a germ count index; the indices denote the following:

Index 0 corresponds to a reduction in the germ count of 0–20% = no action

Index 1 corresponds to a reduction in the germ count of >20–40% = trace action

Index 2 corresponds to a reduction in the germ count of >40–70% = distinct action Index 3 corresponds to a reduction in the germ count of >70–90% = good action Index 4 corresponds to a reduction in the germ count of >90% = very good action In addition to the experiments on mice infected with tuberculosis, experiments were carried out analogously on guinea pigs. In this case, the germ count was determined on the lung homogenate. The animals were infected subcutaneously intrainguinally with Mycobacterium tuberculosis H37Rv and were subjected to therapy once daily from the 14th day after infection over a period of 3 weeks, that is to say 5 times per week. The germ counts were determined in the 4th, 5th and 6th week after infection.

To show the anti-tuberulotic effectiveness of the new carboxylic acid amides, some examples of active compounds according to the invention are tabulated (Tables 1–3).

Table 1

Anti-tuberculotic action of carboxylic acid amides

| Example No. | Minimum inhibitory concentration (on egg medium) in mcg/ml of nutrient medium | | | In vivo action | |
|---|---|---|---|---|---|
| | normally sensitive test strain *Mycobacterium tuberculosis* H37Rv | resistant test strains *Mycobacterium tuberculosis* | | index of reduction in Tb germs | |
| | | INH-res. | INH-TSC-res. | Tb-mice with 100 mg/kg orally subcutaneously | Tb-guinea pigs with 30 mg/kg orally |
| 1 | 1 | 1 | 1 | 4 3 | 4 |
| 13 | 32 | 128 | 128 | 3 2 | 4 |
| 9 | 2 | 2 | 2 | 1 1 | 4 |
| 10 | 1 | 1 | 32 | 2 2 | 3 |
| 12 | 32 | 8 | 32 | 2 2 | 3 |
| 15 | 1 | 1 | 1 | 3 2 | 3 |
| 19 | 2 | 2 | 2 | 2 2 | — |
| 29 | 2 | 2 | 2 | 4 3 | — |

On the Löwenstein-Jensen egg medium, active compounds according to the invention having a good anti-tuberculotic action show an inhibiting action on tubercle bacteria at concentrations of 1 mcg/ml. In the case of mice infected with tuberculosis and guinea pigs infected with tuberculosis, a distinct reduction in the mycobacteria germ count in the spleen and lung of the test animals is found, under therapy, after oral or subcutaneous administration of active compounds according to the invention, which were administered in doses of 100 mg/kg or 30 mg/kg respectively.

bacteria-like microorganisms, fungi, protozoa and viruses. The following can be mentioned as examples: Micrococcaceae, such as Staphylococci; Lactobacteriaceae, such as Streptococci; Mycobacteriaceae, such as tubercle bacteria; Enterbacteriaceae, such as *Escherichia coli*, Klebsiellae and Proteus bacteria; Pseudomonadaceae, such as *Aeromonas* bacteria; parvobacteriaceae, such as Pasteruellae and Bordetella bacteria; Achromobacteriaceae, such as *Alcaligensis faecalis;* Bacillacae, such as *Bacillus substilus;* Mycoplasmae, such as *Mycoplasma gallisepticum;* fungi, such as Trich- Table 2

Anti-tuberculotic action (MIC) against chemo-resistant tubercle bacteria

| | Test strains of *Mycobacterium tuberculosis* | | | | | |
|---|---|---|---|---|---|---|
| Example No. | normally sensitive H37Rv | INH-res. | SM-res. | PAS-res. | CS-res. | INH TSC ETH-res. |
| 1 | 1.6 | 0.8 | 1.6 | 1.6 | 1.6 | 0.8 |
| 9 | 0.2 | 0.4 | 0.2 | 0.4 | 0.2 | 0.03 |
| 14 | 3.1 | 0.8 | 1.6 | 1.6 | 1.6 | 0.8 |
| 15 | 0.2 | 0.1 | 0.1 | 0.4 | 0.2 | 0.05 |
| 22 | 0.4 | 0.1 | 0.4 | 0.8 | 0.4 | 0.2 |
| 20 | 1.6 | 1.6 | 1.6 | 1.6 | 1.6 | 1.6 |
| 19 | 0.8 | 0.8 | 0.4 | 3.1 | 0.8 | 0.2 |
| 29 | 1.6 | 1.6 | 0.8 | 1.6 | 1.6 | 0.8 |

Test medium: modified Difco-Tb-Bouillon
Minimum inhibitory concentration (MIC) in mcg/ml of nutrient medium.

Active compounds according to the invention show a constant effectiveness against mycobacteria which are resistant to various anti-tuberculotic agents, that is to say they do not show any parallel resistance, from which it can be concluded that a different anti-tuberculotic mechanism of action to that of known agents against tuberculosis is involved.

INH = Isoniazid, SM = Streptomycin, PAS = p-aminosalicylic acid, CS = Cycloserine, TSC = thiosemicarbazone, ETH = Ethionamid, res. = resistant, M = Mycobacterium.

ophyton and Microsporon.

The list of pathogens is purely illustrative and is in no way to be interpreted as limiting.

The active compounds according to the invention are outstandingly active against mycobacteria, especially against tubercle bacteria. They are therefore suitable for chemotherapy of mycobacterioses in human medicine and veterinary medicine.

Hitherto, no parallel resistance to commercially available agents against tuberculosis has been found with the active compounds according to the invention.

Table 3

| | Anti-mycobacterial spectrum of action (MIC) | | | | | |
|---|---|---|---|---|---|---|
| | | Test strains of mycobacteria | | | | |
| Example No. | M. tuberculosis H37Rv | M. bovis Ravenal | "Atypical mycobacteria" | | Runyon grouping | |
| | | | Grouping 1 | Grouping 2 | Grouping 3 | Grouping 4 |
| 1 | 1.6 | 3.1 | 6.2 | 6.2 | 50 | 6.2 |
| 9 | 0.2 | 0.4 | 3.1 | 3.1 | >100 | 1.6 |
| 14 | 3.1 | 3.1 | 6.2 | 12.5 | 25 | 12.5 |
| 15 | 0.2 | 0.8 | 1.6 | 6.2 | 1.6 | 1.6 |
| 22 | 0.4 | 3.1 | 1.6 | 1.6 | >100 | 1.6 |
| 20 | 1.6 | 3.1 | 6.2 | 6.2 | 100 | 6.2 |
| 19 | 0.8 | 2.5 | 3.1 | 3.1 | >100 | 1.6 |
| 29 | 1.6 | 3.1 | 3.1 | 3.1 | 100 | 3.1 |

Test medium: modified Difco-Tb-Bouillon
Minimum inhibitory concentration (MIC) in mcg/ml of nutrient medium The compounds of the present invention exhibit both an inhibition as to *M. tuberculosis* and an antimycobacterial action of about the same order of magnitude against *M. bovis* as well as the so-called "atypical mycobacteria" of Runyon groupings 1, 2 and 4. The effectiveness against Runyon group 3 is low with partial resistance.

The new active compounds exhibit a low toxicity and a powerful antimicrobial activity. These properties permit their use as chemotherapeutic active compounds in human medicine and veterinary medicine, especially in the case of domestic animals, for example cows.

At high concentrations, the active compound are also active against a large number of microorganisms, including Gram-positive and Gram-negative bacteria, As a result of the different mechanism of action which this indicates, the new active compounds offer advantages for the composition (essential in tuberculosis therapy) of combinations of medicaments of specific anti-tuberculosis activity.

The spectrum of action of the compounds according to the invention also embraces so-called atypical mycobacteria, which increasingly cause mycobacterioses which have hitherto been difficult to treat by chemotherapy.

As stated above, the invention also relates to the use in human and veterinary medicine of the compounds of the invention.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

In general satisfactory antibacterial effects are obtained when the compounds are administered in doses of from about 20 mg to about 200, preferably 30 to 100, mg/kg of body weight per day. An individual administration preferably contains an active compound according to the invention in an amount of from 6.5 to 60, preferably 10 to 33 mg/kg of body weight. Nevertheless, it will at times be necessary to deviate from those dosage rates, and in particular to do so as a function of the nature and body weight of the animal being treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, while in other cases the upper limit mentioned must be exceeded to achieve the desired results. Where larger amounts are administered it can be advisable to divide these into several individual administrations over the course of the day.

The following examples will serve to further illustrate the nature of the invention without being a limitation on the scope thereof, the scope being defined solely by the appended claims.

EXAMPLE 1

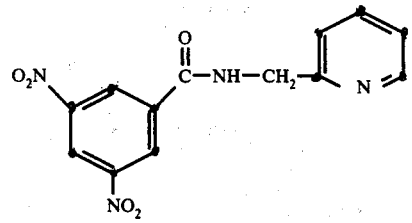

A solution of 46 g of 3,5-dinitrobenzoyl chloride in 200 ml of toluene was added to a solution of 25 g of α-aminomethylpyridine, 30 ml of triethylamine and 100 ml of toluene over the course of 10 minutes at 15°–20° C (ice bath). The mixture was stirred for a further 2 hours at room temperature, 400 ml of half-concentrated sodium carbonate solution and 400 ml of petroleum ether were added, the mixture was stirred for a further hour and the product was filtered off, using a large amount of water. After drying, 42 g (70% of theory) of N-(pyrid-2-ylmethyl)-3,5-dinitrobenzoic acid amide of melting point 172°–173° C were obtained.

By treating the batch in the manner indicated but without the addition of triethylamine and sodium carbonate solution, the hydrochloride of N-(pyrid-2-ylmethyl)-3,5-dinitrobenzoic acid amide, of melting point 226°–227° C, was obtained in a yield of 75% of theory.

EXAMPLE 2

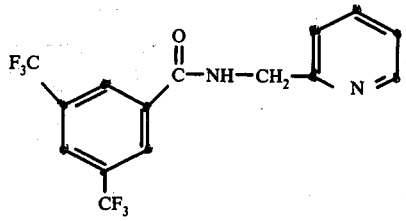

4.4 g of dicyclohexylcarbodiimide were added to a solution of 5.64 g of 3,5-bis(trifluoromethyl)benzoic acid in 50 ml of toluene. 2.4 g of α-aminomethylpyridine were then added, the mixture was stirred for 20 hours at 25° C and the dicyclohexylurea which had precipitated was filtered off. The mother liquor was concentrated and the residue was recrystallized from toluene. 6.2 g (86% of theory) of N-(pyrid-2-ylmethyl)-3,5-bis(trifluoromethyl)benzoic acid amide of melting point 123°–124° C were thus obtained.

EXAMPLE 3

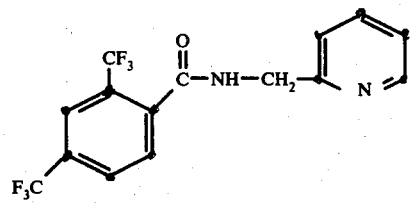

5.4 g of 2,4-bis(trifluoromethyl)benzoic acid methyl ester and 2.5 g of 2-aminomethylpyridine were heated to 160°–180° C for 6 hours. After cooling, the product was recrystallized from toluene. 4.2 g (64% of theory) of N-(pyrid-2-ylmethyl)-2,4-bis(trifluoromethyl)benzoic acid amide of melting point 112°–113° C were thus obtained.

EXAMPLE 4

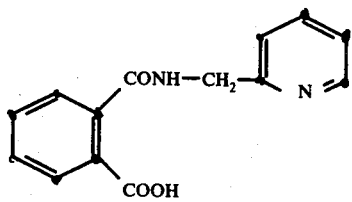

A solution of 35 g of phthalic anhydride in 150 ml of dioxane was added to a solution of 25 g of α-aminomethylpyridine in 50 ml of toluene. The temperature was kept below 35° C by cooling with ice. After about 2 hours, the precipitate formed was filtered off. 59 g (92% of theory) of N-(pyrid-2-ylmethyl)-2-carboxybenzoic acid amide of melting point 140–142° C were obtained.

EXAMPLE 5

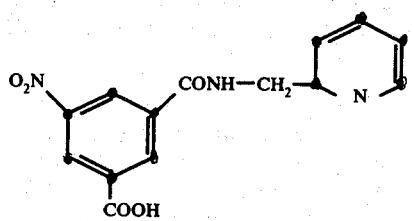

12.6 g of N-(pyrid-2-ylmethyl)-3-carbomethoxy-5-nitrobenzoic acid amide were dissolved in 150 ml of methanol and 150 ml of acetone. 25 ml of 2 N NaOH were added to the mixture, the whole was left to stand for 1 day at 25° C and concentrated, the precipitate was dissolved in water and the solution was acidified, whereupon 9.2 g (78% of theory) of N-(pyrid-2-ylmethyl)-3-carboxy-5-nitrobenzoic acid amide were obtained.

EXAMPLE 6

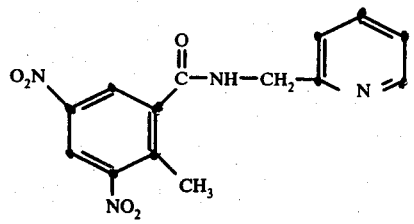

4.34 g (0.01 mol) of 2-methyl-3,5-dinitrobenzoic anhydride (obtained as a by-product, of melting point 245° C, from the reaction of 2-methyl-3,5-dinitrobenzoic acid with thionyl chloride) and 1.08 g (0.01 mol) of 2-aminomethylpyridine in 25 ml of ethanol were heated to the boil for 15 minutes. On cooling, N-(pyrid-2-ylmethyl)-3,5-dinitro-2-methylbenzoic acid amide crystallized out from the clear solution. After filtering off, washing with sodium carbonate solution and recrystallizing from ethanol, the yield was 2.5 g (83% of theory) of melting point 151°–152° C.

The other carboxylic acid amides (Examples 7–49 in Table 4 which follows) were prepared analogously to Example 1, that is to say using triethylamine as the acid-binding base, in toluene. The mixtures were worked up with sodium carbonate solution (A) or with water (B).

Table 4

| Example No. | R | $R^1$ | $R^2$ | $R^3$ | $R^4$ |
|---|---|---|---|---|---|
| 7 | 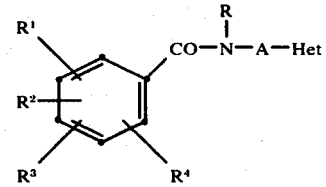 | 3-$NO_2$ | 5-$NO_2$ | H | H |
| 8 | $C_2H_5$ | 3-$NO_2$ | 5-$NO_2$ | H | H |

Table 4-continued

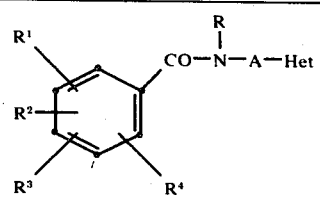

| Example No. | R | R¹ | R² | R³ | R⁴ |
|---|---|---|---|---|---|
| 9 | H | 3-NO₂ | 5-NO₂ | H | H |
| 10 | H | 3-NO₂ | 5-NO₂ | H | H |
| 11 | H | 3-NO₂ | 5-NO₂ | H | H |
| 12 | H | 3-NO₂ | 5-NO₂ | H | H |
| 13 | H | 3-NO₂ | 5-NO₂ | H | H |
| 14 | H | 3-NO₂ | 5-NO₂ | H | H |
| 15 | H | 3-NO₂ | 5-NO₂ | H | H |
| 16 | H | 3-NO₂ | 5-NO₂ | H | H |
| 17 | H | 3-NO₂ | 5-NO₂ | H | H |
| 18 | (2-pyridyl)-CH₂- | 3-NO₂ | 5-NO₂ | H | H |
| 19 | H | 3-NO₂ | 5-NO₂ | H | H |
| 20 | H | 3-NO₂ | 5-NO₂ | H | H |
| 21 | H | 3-NO₂ | 5-NO₂ | H | H |
| 22 | H | 3-NO₂ | 5-NO₂ | H | H |
| 23 | H | 3-NO₂ | 5-NO₂ | H | H |
| 24 | H | 3-NO₂ | 5-NO₂ | H | H |
| 25 | H | 3-NO₂ | 5-NO₂ | H | H |
| 26 | CH₃ | 3-NO₂ | 5-NO₂ | H | H |
| 27 | H | 3-NO₂ | 5-NO₂ | H | H |
| 28 | H | 3-NO₂ | 5-NO₂ | H | H |
| 29 | H | 3-NO₂ | 5-NO₂ | H | H |
| 30 | H | 2-NO₂ | 4-NO₂ | H | H |
| 31 | H | 3-NO₂ | 5-COOCH₃ | H | H |
| 32 | H | 3-NO₂ | 5—CONH—CH₂-(2-pyridyl) | H | H |
| 33 | H | 3-NO₂ | 5-NO₂ | 6-Cl | H |
| 34 | H | 3-NO₂ | 5-CF₃ | H | H |
| 35 | H | 3-NO₂ | 5-NO₂ | 2-Cl | 6-Cl |
| 36 | H | 3-NO₂ | H | 2-CH₃ | 5-Cl |
| 37 | H | 3-NO₂ | H | H | H |
| 38 | H | 3-CF₃ | H | H | H |
| 39 | H | 2-NO₂ | H | H | 3-Cl |
| 40 | H | 4-NO₂ | H | H | H |
| 41 | H | 4-CF₃ | H | H | H |
| 42 | H | 2-CF₃ | H | H | H |
| 43 | H | 3-CH₃SO₂- | H | H | 6-Cl |
| 44 | H | 3-NO₂ | H | H | 5-Br |
| 45 | H | 3-NO₂ | 5-NO₂ | H | H |

Table 4-continued
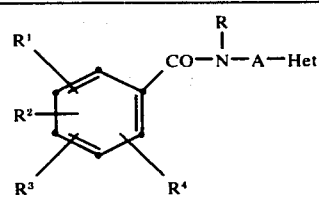
| Example No. | R | R¹ | R² | R³ | R⁴ |
|---|---|---|---|---|---|
| 46 | H | 3-CN | H | H | H |
| 47 | H | 3-COOCH₃ | H | H | H |
| 48 | H | 3-NO₂ | H | H | 4-Cl |
| 49 | H | 3-CF₃ | H | H | H |
| 50 | H | 3-CN | 5-NO₂ | H | H |
| 51 | H | 3-NO₂ | 5-NO₂ | H | H |
| 52 | H | 3-NO₂ | 5-NO₂ | H | H |
| 53 | H | 3-NO₂ | 5-NO₂ | H | H |
| 54 | H | 3-NO₂ | 5-NO₂ | H | H |
| 55 | H | 3-CN | H | H | H |
| Example No. | A | Het | Working up | Yield (% of theory) | Melting point (° C) |
|---|---|---|---|---|---|
| 7 | —CH₂— | pyridine | B | 74 | 102–4 |
| 8 | —CH₂— | pyridine | A | 43 | 97–8 |
| 9 | —CH₂— | quinoline | A | 81 | 258–60 |
| 10 | —CH₂—CH₂— | pyridine | B | 98 | 127–9 |
| 11 | —CH₂— | furan | A | 63 | 151–3 |
| 12 | —CH₂— | pyridine | A | 80 | 193–4 |
| 13 | —CH₂— | pyridine | A | 69 | 177–9 |
| 14 | —CH₂— | 2,6-dimethylpyridine | A | 54 | 160–1 |
| 15 | —CH₂— | 2-methylquinoline | B | 99 | 208–209 |

Table 4-continued

| Example No. | A | Het | Working up | Yield (% of theory) | Melting point (° C) |
|---|---|---|---|---|---|
| 16 | —CH— \| C₆H₅ | pyridin-2-yl | A | 55 | 156–8 |
| 17 | —CH₂— | 5-(3,4-dichlorophenyl)-furan-2-yl | B | 57 | 159–61 |
| 18 | —CH₂— | pyridin-2-yl | B | 56 | 122–4 |
| 19 | —CH₂—CH₂—CH₂— | pyridin-N-yl | B | 69 | 90–2 |
| 20 | —CH₂— | tetrahydrofuran-2-yl | B | 71 | 124–6 |
| 21 | —CH₂—CH₂— | furan-2-yl | B | 58 | 105–7 |
| 22 | —CH₂— | tetrahydropyran-2-yl | B | 86 | 113–5 |
| 23 | CH₃ \| —CH— | furan-2-yl | B | 63 | 165–7 |
| 24 | —CH₂— | 3-methyl-1,2,3,4-tetrahydroquinolin-yl | B | 61 | 238 |
| 25 | —CH₂—CH₂— | indol-3-yl | A | 66 | 253–5 |
| 26 | —CH₂— | 5-methylfuran-2-yl | B | 53 | 81–3 |
| 27 | —CH₂— | benzimidazol-2-yl | A | 81 | 258–60 |
| 28 | —CH₂—CH₂— | 4-methylthiazol-2-yl | B | 70 | 240–3 |

Table 4-continued
| Example No. | A | Het | Working up | Yield (% of theory) | Melting point (°C) |
|---|---|---|---|---|---|
| 29 | —CH—<br>\|<br>CH₃ | 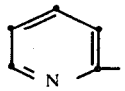 | B | 84 | 134–5 |
| 30 | —CH₂— | 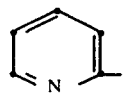 | A | 84 | 187–8 |
| 31 | —CH₂— | 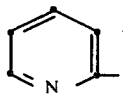 | B⁽¹⁾ | 79 | 136–8 |
| 32 | —CH₂— | 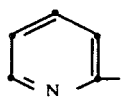 | A | 62 | 163–5 |
| 33 | —CH₂— | 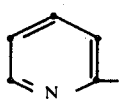 | A | 96 | 150 |
| 34 | —CH₂— |  | A | 85 | 140–2 |
| 35 | —CH₂— |  | B | 74 | 199–200 |
| 36 | —CH₂— | 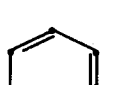 | A | 47 | 111–3 |
| 37 | —CH₂— |  | A | 71 | 88–90 |
| 38 | —CH₂— |  | A | 87 | 55–57 |
| 39 | —CH₂— |  | A | 66 | 157–8 |
| 40 | —CH₂— | 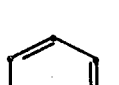 | A | 93 | 127–9 |
| 41 | —CH₂— | 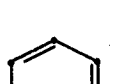 | A | 71 | 104–6 |

Table 4-continued

| Example No. | A | Het | Working up | Yield (% of theory) | Melting point (° C) |
|---|---|---|---|---|---|
| 42 | —CH₂— | pyridine | B | 69 | 96–8 |
| 43 | —CH₂— | pyridine | B | 51 | 167–8 |
| 44 | —CH₂— | pyridine | A | 73 | 163–5 |
| 45 | —CH₂—CH₂— | triazole (N=N, CH=CH) | A | 59 | 238–40 |
| 46 | —CH₂— | pyridine | A | 69 | 181–3 |
| 47 | —CH₂— | pyridine | A | 84 | 111–3 |
| 48 | —CH₂— | pyridine | A | 56 | 160–2 |
| 49 | —CH₂— | pyridine | A | 49 | 70–2 |
| 50 | —CH₂— | pyridine | A | 68 | 158–159° |
| 51 | —CH₂— | pyrimidine | A | 35 | 196–197° |
| 52 | —CH₂— | isoquinoline | A | 45 | 206–207° |
| 53 | —CH₂— | indole | A | 51 | 249° |

Table 4-continued

| Example No. | A | Het | Working up | Yield (% of theory) | Melting point (° C) |
|---|---|---|---|---|---|
| 54 | —CH₂—CH₂— | 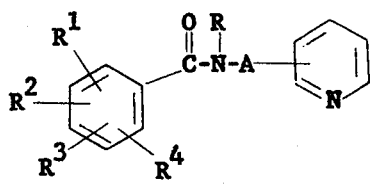 | A | 80% | 186–188° |
| 55 | —CH₂— | | A | 68° | 114–115° |

⁽¹⁾The acid chloride used in Example 31 is known from the literature [J.Med.Chem. 6, 24,(1963)]

What is claimed is:

1. The method of combatting Mycobacterium infections in humans and other animals which comprises administering parenterally or orally to said human or other animal from about 20 mg to about 200 mg/kg of a compound of the formula:

$$\begin{array}{c} R^1 \\ R^2 \end{array} \begin{array}{c} O\ R \\ \|\ | \\ C-N-A \end{array} \begin{array}{c} \\ \\ N \end{array}$$

wherein R is hydrogen, methyl, ethyl, benzyl or pyridylmethyl;
R¹ is nitro, cyano, trifluoromethyl, methylsulfonyl, carboxy, carbomethoxy or carbethoxy;
R² is hydrogen, nitro, cyano, trifluoromethyl, methylsulfonyl, carboxy, carbomethoxy or carbethoxy;
each of R³ and R⁴, independent of the other, is hydrogen, chloro, bromo or methyl; and
A is methylene, ethylene, ethylidene, trimethylene or benzylidene.

2. The method according to claim 1 wherein said compound is administered in combination with a pharmaceutically acceptable nontoxic carrier.

3. The method according to claim 1 in which said compound is N-[2-(pyrid-2-yl)ethyl]-3,5-dinitrobenzoic acid amide.

4. The method according to claim 1 in which said compound is N-[1-(pyrid-2-yl)ethyl]-3,5-dinitrobenzoic acid amide.

5. The method according to claim 1 in which said compound is N-(pyrid-2-ylmethyl)-3,5-dinitrobenzoic acid amide.

6. The method according to claim 1 in which said compound is N-(pyrid-2-ylmethyl)-3-carboxybenzoic acid amide.

7. The method according to claim 1 in which said compound is N-(pyrid-3-ylmethyl)-3,5-dinitrobenzoic acid amide.

8. The method according to claim 1 in which said compound is N-(pyrid-4-ylmethyl)-3,5-dinitrobenzoic acid amide.

9. The method according to claim 1 in which said compound is N-(2-methylpyrid-6-ylmethyl)-3,5-dinitrobenzoic acid amide.

10. The method according to claim 1 in which said compound is N-(pyrid-2-ylmethyl)-3-cyanobenzoic acid amide.

11. The method according to claim 1 in which said compound is N-(pyrid-2-ylmethyl)-3-carbomethoxybenzoic acid amide.

* * * * *